United States Patent [19]

Ratcliffe et al.

[11] Patent Number: 4,798,816

[45] Date of Patent: Jan. 17, 1989

[54] PROCESS FOR INCREASING THE SELECTIVITY OF AN ALKYLATION CATALYST FOR MONOALKYLATION

[75] Inventors: Charles T. Ratcliffe, La Habra; John W. Ward, Yorba Linda, both of Calif.

[73] Assignee: Union Oil Company of California, Los Angeles, Calif.

[21] Appl. No.: 943,911

[22] Filed: Dec. 19, 1986

[51] Int. Cl.$^4$ .................. B01J 29/06; B01J 29/02
[52] U.S. Cl. ........................... 502/62; 502/52
[58] Field of Search ............... 502/62, 52; 585/467

[56] References Cited

U.S. PATENT DOCUMENTS

| | | | |
|---|---|---|---|
| 3,069,363 | 12/1962 | Mays et al. | 502/52 |
| 3,525,775 | 8/1970 | Bolton et al. | 502/62 |
| 3,676,330 | 7/1972 | Plank et al. | 502/64 |
| 4,001,346 | 1/1977 | Chu | 585/467 |
| 4,085,156 | 4/1978 | Frilette et al. | 208/120 |
| 4,157,950 | 6/1979 | Frilette et al. | 208/135 |
| 4,185,040 | 1/1980 | Ward et al. | 585/467 |
| 4,231,899 | 11/1980 | Chen et al. | 502/62 |
| 4,300,014 | 11/1981 | Yamasaki et al. | 502/52 |
| 4,358,395 | 11/1982 | Haag et al. | 585/467 |
| 4,387,259 | 6/1983 | Barile | 585/467 |
| 4,508,836 | 4/1985 | Haag et al. | 585/467 |
| 4,570,027 | 2/1986 | Boucher et al. | 585/455 |
| 4,600,700 | 7/1986 | McHale | 502/52 |

*Primary Examiner*—Carl F. Dees
*Attorney, Agent, or Firm*—Yale S. Finkle; Gregory F. Wirzbicki

[57] ABSTRACT

A process for treating a molecular sieve-containing alkylation catalyst to increase its selectivity for monoalkylation in which the alkylation catalyst is contacted with a feedstock comprising at least one organic compound under conditions such that a sufficient amount of carbonaceous material evenly deposits on the alkylation catalyst to substantially suppress its alkylation activity. The carbon-containing catalyst particles are then subjected to combustion by contacting them with a gaseous oxidizing agent at an elevated temperature to remove at least a portion of the carbonaceous material, preferably substantially all of the carbonaceous material, thereby increasing the selectivity of the catalyst for monoalkylation by at least about 1.0 percentage point. The resulting alkylation catalyst can be used to alkylate benzene and other aromatic compounds with ethylene, propylene or other olefins to produce high yields of ethylbenzene, cumene and other alkylated products. Preferably, the alkylation catalyst contains an ammonium-exchanged and steam stabilized Y zeolite.

38 Claims, No Drawings

PROCESS FOR INCREASING THE SELECTIVITY OF AN ALKYLATION CATALYST FOR MONOALKYLATION

BACKGROUND OF THE INVENTION

This invention relates to the alkylation of aromatic compounds and is particularly concerned with (1) a process for increasing the selectivity of an alkylation catalyst for monoalkylation, (2) alkylation catalysts that have been treated in such a manner as to improve their selectivity for monoalkylation and (3) alkylation processes using such catalysts of improved selectivity for monoalkylation.

In the past it has been common practice to alkylate aromatic molecules such as benzene, toluene and xylene with ethylene, propylene and other olefins using acidic Friedel-Crafts type catalysts or heterogeneous acidic silica-alumina catalysts. Such processes have several disadvantages including corrosion problems caused by Friedel-Crafts type catalysts and difficulty in controlling the product distribution obtained from the alkylation reactions. Normally, the desired product is the monoalkylate rather than the di or trialkylate. In an effort to avoid a large production of di and trialkylate products, it is conventional practice to use a large excess of the aromatic compound.

To avoid some of the problems associated with earlier commercial alkylation processes, solid zeolite-containing catalysts have been used in recent years to promote the alkylation of aromatic compounds with olefins and other alkylating agents, especially the alkylation of benzene with ethylene. Normally, these catalysts are used in a fixed bed reactor through which the reactants are continuously passed. Although such fixed bed processes using zeolite-containing catalysts have advantages over earlier commercial processes, the selectivity and activity maintenance for monoalkylation, especially when producing cumene by reacting propylene with benzene, is not as high as desired and is often unsatisfactory.

Accordingly, it is one of the objects of the present invention to provide a process for increasing the selectivity and maintaining the activity of alkylation catalysts containing zeolites and other molecular sieves. It is another object of the invention to provide a molecular sieve-containing alkylation catalyst having an increased selectivity for monoalkylation and a process for alkylating an aromatic compound to form an alkylated aromatic using a catalyst having an increased selectivity for monoalkylation. These and other objects of the invention will become more apparent in view of the following description of the invention.

SUMMARY OF THE INVENTION

In accordance with the invention it has now been found that the selectivity of a molecular sieve-containing alkylation catalyst can be increased by at least about 1.0 percentage point while maintaining a relatively high activity by depositing carbonaceous material on the catalyst and then subjecting the resultant carbon-containing catalyst particles to combustion. The carbon deposition step is normally carried out by contacting the alkylation catalyst with a feedstock comprising at least one organic compound under conditions such that a sufficient amount of carbonaceous material deposits relatively evenly on the alkylation catalyst to suppress its alkylation. The carbon-containing catalyst particles are then treated with a gaseous oxidizing agent at an elevated temperature to remove at least a portion, normally greater than about 95 weight percent, of the carbonaceous material. The resulting alkylation catalyst exhibits a much higher selectivity for monoalkylation than it did prior to its treatment in accordance with above-described process of the invention. As used herein the term "selectivity" refers to the ratio multiplied by 100 of the molar amount of the desired monoalkylated product and the molar amount of all products derived from the alkylating agent. In addition to exhibiting a high selectivity, the treated catalyst wil possess an activity maintenance at least about 95 percent, typically about 100 percent, that of the catalyst prior to treatment in accordance with the invention.

In a preferred embodiment of the invention, the feedstock with which the alkylation catalyst is contacted is a hydrocarbon feedstock, preferably one comprising a mixture of benzene and propylene. The alkylation catalyst is normally present in the contacting zone in the form of a fixed bed and the catalyst is typically contacted with the hydrocarbon feedstock until the reaction exotherm zone has passed through the fixed bed of catalyst, thereby indicating that the catalyst has been deactivated by the relatively uniform deposition of carbonaceous material on the catalyst particles. The carbon-containing catalyst particles are then preferably treated with a gaseous oxidizing agent in two stages. First, the catalyst particles are contacted with a gas comprising between about 0.05 and about 5.0 volume percent oxygen, preferably between about 0.2 and about 1.0 volume percent, as the temperature is gradually increased from at least ambient temperature, preferably from a temperature between about 25° F. and about 100° F. to a temperature in the range between about 750° F. and about 1100° F., preferably between about 750° F. and about 950° F., and most preferably between about 800° F. and about 875° F., to remove a portion but not all of the carbonaceous material via combustion. After combustion in this first stage ceases, the oxygen concentration of the gas is increased at least about 0.01 percentage point, preferably at least about 0.05 percentage point, and the temperature is gradually increased to a value between about 850° F. and about 1200° F., preferably between about 900° F. and about 1000° F., while contacting is continued until substantially all of the carbonaceous material is combusted. The resulting alkylation catalyst has been found to have a substantially higher selectivity for monoalkylation than the catalyst originally placed in the fixed bed contacting zone.

In a preferred embodiment of the invention, the molecular sieve-containing alkylation catalyst subjected to the process of the invention contains a Y zeolite, preferably a steam treated and stabilized zeolite known as LZY-82 zeolite. Tests indicate that the process of the invention can increase the selectivity of such a catalyst for the alkylation of benzene with propylene to form cumene from about 94.6 percent to about 97.6 percent.

DETAILED DESCRIPTION OF THE INVENTION

The molecular sieve-containing alkylation catalyst that can be treated in accordance with the process of the invention to increase its selectivity for monoalkylation will normally comprise a zeolitic or nonzeolitic molecular sieve composited with a porous, inorganic refractory oxide matrix or binder. The term "nonzeolitic" as used herein refers to molecular sieves whose frameworks are not formed of substantially only silica and alumina tetrahedra. The term "zeolitic" as used herein refers to molecular sieves whose frameworks are formed of substantially only silica and alumina tetrahedra such as the framework present in ZSM-5 type zeolites, Y zeolites and X zeolites.

Examples of porous, inorganic refractory oxide components which can be used as the binder or matrix include alumina, gallia, thallia, titania, zirconia, beryllia, silica, silica-alumina, silica-magnesia, magnesia, silica-titania, other such combinations and the like. Examples of nonzeolitic crystalline molecular sieves which may serve as the active alkylation component of the catalyst include silicoaluminophosphates, aluminophosphates, ferrosilicates, chromosilicates, borosilicates, and crystalline silicas such as silicalite. The zeolitic crystalline molecular sieves which can be used as the active alkylation component of the catalyst may be selected from the group of Y zeolites, fluorided Y zeolites, X zeolites, zeolite beta, zeolite L, zeolite omega and modifications of such zeolites. In general, the alkylation catalyst will contain between about 2 and about 98 weight percent molecular sieve, preferably between about 50 and about 95 weight percent, while the amount of binder or matrix in the catalyst will range between about 2 and about 98 weight percent, preferably between about 5 and about 50 weight percent.

The most preferred molecular sieves for use as the active alkylation component of the catalysts which may be treated in accordance with the process of the invention are Y zeolites. U.S. Pat. No. 3,130,007, the disclosure of which is hereby incorporated by reference in its entirety, describes Y-type zeolites having an overall silica-to-alumina mole ratio between about 3.0 and about 6.0, with a typical Y zeolite having an overall silica-to-alumina mole ratio of about 5.0. It is also known that Y-type zeolites can be produced, normally by dealumination, having an overall silica-to-alumina mole ratio above 6.0. Thus, for purposes of this invention, a Y zeolite is one having the characteristic crystal structure of a Y zeolite, as indicated by the essential X-ray powder diffraction pattern of Y zeolite, and an overall silica-to-alumina mole ratio above 3.0, and includes Y-type zeolites having an overall silica-to-alumina mole ratio above 6.0.

A preferred Y zeolite for use as the molecular sieve component of the alkylation catalysts which may be treated in accordance with the process of the invention is one produced by (1) first ammonium exchanging a Y zeolite to a sodium content between about 0.6 and 5.0 weight percent, calculated as $Na_2O$; (2) calcining the ammonium-exchanged zeolite at a temperature between about 600° F. and 1650° F. in the presence of steam at a water vapor partial pressure of at least 0.2 p.s.i.a., preferably above about 2.0 p.s.i.a., and most preferably between about 5.0 and about 15 p.s.i.a., to reduce the unit cell size of the ammonium-exchanged zeolite to a value in the range between about 24.40 and 24.64 Angstroms, and then (3) ammonium exchanging the steam calcined zeolite to replace at least 25 percent of the residual sodium ions and obtain a zeolite product of less than about 1.0 weight percent sodium, preferably less than about 0.6 weight percent sodium, and most preferably below about 0.2 weight percent sodium, calculated as $Na_2O$. Such a Y zeolite is highly stable and maintains a high activity. The zeolite is described in detail in U.S. Pat. No. 3,929,672, the disclosure of which is hereby incorporated by reference in its entirety. The same or a substantially similar zeolite is sold by the Linde Division of Union Carbide Corporation as LZY-82 zeolite.

The alkylation catalyst which is subjected to the process of the invention can be either a fresh catalyst, i.e., one that has not previously been used to alkylate an aromatic compound, or a deactivated or partially deactivated alkylation catalyst, i.e., one that has already been used to at least some degree for promoting the alkylation of an aromatic compound. Since the process of the invention is quite effective in increasing the selectivity of a fresh alkylation catalyst, it may be desirable to subject a fresh catalyst to the process of the invention before it is used commercially to alkylate aromatic compounds.

The alkylation catalyst is subjected to the process of the invention by first contacting the catalyst with a feedstock comprising at least one organic compound under conditions such that carbonaceous material deposits relatively evenly on the catalyst, thereby suppressing its alkylation activity. The feedstock utilized is preferably a hydrocarbon feedstock. As used herein "hydrocarbon" refers to any compound which comprises hydrogen and carbon and "hydrocarbon feedstock" refers to any charge stock which contains a mixture of hydrocarbon compounds and comprises greater than about 70 weight percent carbon and hydrogen, preferably greater than about 80 weight percent, calculated as the elements. Examples of hydrocarbon feedstocks that may be used in the process of the invention include nonpolar aromatic compounds such as benzene, toluene, ethylbenzene and xylene, unsaturated aliphatic hydrocarbons such as alkenes and alkynes, preferably $C_2$–$C_{15}$ alkenes or alkynes, and polar aliphatic hydrocarbons such as alcohols and alkyl halides. The preferred hydrocarbon feedstocks will normally comprise a mixture of an aromatic compound such as benzene and an unsaturated aliphatic hydrocarbon such as ethylene or propylene.

In order to effectively suppress the alkylation activity of the catalyst, the hydrocarbon feedstock is contacted with the catalyst, normally by passing the feedstock through a fixed bed of the catalyst, under conditions such that carbonaceous material deposits on the alkylation catalyst. When a mixture of a nonpolar aromatic compound such as benzene or toluene and an unsaturated aliphatic hydrocarbon, preferably an olefin, is used as the hydrocarbon feedstock, the temperature at which the feedstock and catalyst are contacted will normally range between about 250° F. and about 800° F., preferably between about 350° F. and about 500° F. The pressure in the contacting zone will typically range between about 150 p.s.i.g. and about 2000 p.s.i.g. The mole ratio of the olefin to the aromatic compound in the feedstock will normally range from about 0.01 to 10.0. In general, the conditions in the contacting zone are held relatively constant until the reaction exotherm zone, i.e., the exotherm caused by the reaction of the aromatic compound with the olefin, passes through the entire catalyst bed. The passage of the exotherm zone through the bed can be monitored by following the catalyst bed temperature profile. Passage of the exotherm zone through the entire catalyst bed is indicative of the fact that tars, i.e., carbonaceous material comprising condensed aromatics and olefin polymers, have been uniformly deposited over the alkylation catalyst to suppress its alkylation activity.

After the alkylation catalyst has been treated in accordance with the procedure discussed above, the carbon-containing catalyst particles are subjected to a combustion step by contacting the particles with a gaseous oxidizing agent at a temperature between about 550° F. and about 1100° F., preferably between about 800° F. and about 950° F., to remove at least a portion of the deposited carbonaceous material. It has been surprisingly found that the resultant carbon-depleted material has an activity maintenance and a selectivity that are, respectively, at least 95 percent of and at least about 1.0 percentage point greater than the activity maintenance and selectivity of the fresh, deactivated or partially deactivated alkylation catalyst which is subjected to treatment in accordance with the process of the invention. It is normally preferred to carry out the combustion step under conditions such that greater than about 95 percent, preferably greater than about 98 weight percent, of the carbonaceous material is removed from the catalyst. It is most preferred that the combustion step be carried out under conditions such that substantially all of the carbonaceous material is removed from the catalyst.

The above-described combustion step is typically carried out in situ in a fixed bed alkylation reactor by passing the gaseous oxidizing agent through the particles of carbon-containing catalyst. It will be understood, however, that the combustion step can be conducted in a separate vessel which can be a fixed bed or fluidized bed combustor, a rotary calciner, a moving belt combustor and the like. The gaseous oxidizing agent may be oxygen, air, carbon dioxide, steam, nitrogen dioxide, nitric oxide, nitrous oxide, and mixtures thereof. Preferably, however, the gaseous oxidizing agent comprises oxygen in amounts ranging between about 0.05 and about 60 volume percent, preferably between about 0.05 and about 5.0 volume percent. The most preferred gaseous oxidizing agent is air diluted with nitrogen, a combustion gas or steam so that the oxygen content of the resultant gas is between about 0.2 and about 1.0 volume percent.

In a preferred embodiment of the combustion step, the carbonaceous material is burned from the treated catalyst particles in two stages. In the first stage the carbon-containing catalyst particles are contacted with a gaseous oxidizing agent comprising between about 0.05 and about 5.0 volume percent oxygen, preferably between about 0.2 and about 1.0 volume percent, as the temperature is gradually increased from at least ambient temperature, preferably from a temperature between about 25° F. and about 100° F. to a temperature between about 750° F. and about 1100° F., preferably between about 750° F. and about 950° F., and most preferably between about 800° F. and about 875° F., to remove a portion but not all of the carbonaceous material on catalyst particles. After combustion in this first stage ceases, the oxygen concentration of the gas is increased at least about 0.01 percentage point, preferably at least about 0.05 percentage point, and the temperature is gradually increased to a value between about 850° F. and about 1200° F., preferably between about 900° F. and about 1000° F., while contacting is continued until substantially all of the carbonaceous material is combusted. In both stages of contacting, the temperature increase is limited such that the exothermic temperature rise caused by combustion of carbon on the catalyst particles does not exceed 200° F., preferably 100° F., and most preferably 25° F.

During the combustion step it is necessary to avoid extremely high temperatures so that the crystallinity of the molecular sieve component of the alkylation catalyst is not destroyed. Preferably, the combustion step is carried out under conditions such that there is substantially no decrease in the crystallinity of the molecular sieve, i.e., the molecular sieve is collapsed during the combustion step by less than about 10 percent as compared to the crystallinity of the molecular sieve in the alkylation catalyst subjected to the process of the invention, preferably less than about 5 percent, as measured by X-ray diffraction.

In the embodiment of the invention described above, a fresh, partially deactivated or completely deactivated alkylation catalyst is first contacted with a hydrocarbon feedstock under conditions such that the activity of the catalyst is suppressed by the uniform deposition of carbonaceous material and then subjected to combustion to remove the deposited carbonaceous material. The resultant alkylation catalyst has a higher selectivity for monoalkylation than the original catalyst prior to treatment in accordance with the invention. It will be understood that the first step in the process of the invention may not be necessary when treating a completely deactivated alkylation catalyst if the catalyst has been used in an alkylation process under conditions such that its activity was suppressed by the uniform distribution of carbonaceous material throughout the catalyst bed. If this is the case, it may only be necessary to subject the deactivated catalyst to the combustion step described above in order to significantly increase its selectivity for monoalkylation.

The catalyst of the invention, which is produced in accordance with the process described above, will have a marked increase in selectivity for monoalkylation. This increase will normally be at least 1.0 percentage point higher than that obtained with a catalyst of the same composition which has not been treated in accordance with process of the invention, typically at least about 2.0 percentage points higher, and in many cases at least about 3.0 percentage points higher. In a specific case, it has been found that the selectivity of a catalyst containing 90 weight percent LZY-82 zeolite and 10 weight percent Catapal alumina for producing cumene from benzene and propylene was 94.6 percent while the cumene selectivity for the same catalyst treated in accordance with the process of the invention was 97.6 percent, an increase of 3 percentage points.

The shape of the catalyst of the invention is essentially the same as the shape of the catalyst subjected to the process of the invention. Although the catalyst may be cylindrical in shape, it is normally preferred that the catalyst be in the shape of three-leaf clovers similar to the shape shown in FIGS. 8 and 8A of U.S. Pat.No. 4,028,227, the disclosure of which is hereby incorporated by reference in its entirety. It is normally desired that the catalyst particles have a surface-to-volume ratio greater than that of particles in the shape of a cylinder and preferably in the range between about 85 and about 160 reciprocal inches. Normally, the length of the catalyst particles ranges between about 0.01 and 0.25 inch and the diameter between about 0.03 and 0.08 inch. The preferred shapes of the catalyst particles are described in detail in U.S. Pat. No. 4,185,040, the disclosure of which is hereby incorporated by reference in its entirety.

The catalyst of the invention may be used to increase the selectivity for monoalkylation when alkylating an aromatic compound with an alkylating agent in any conventional manner. The aromatic compound that is alkylated may be a monocyclic aromatic compound such as benzene or toluene, a polycyclic aromatic compound such as naphthalene, methyl naphthalene or anthracene, and nonpolar substituted derivatives of such monocyclic and polycyclic aromatic compounds. The alkylating agent used may be any aliphatic compound capable of reacting with the aromatic compound used. Normally, the alkylating agent will be a $C_2$–$C_{35}$ olefin, preferably a $C_2$–$C_{25}$ olefin, most preferably ethylene, propylene, isobutene or n-butene. Usually a monoalkylated product is desired, but polyalkylated products can also be produced by, for instance, using toluene as the aromatic compound and ethylene as the alkylating agent. The process of the invention, however, is preferably used to produce ethylbenzene from benzene and ethylene, most preferably to produce cumene from benzene and propylene. Regardless of what aromatic compound or alkylating agent is utilized, use of the catalyst of the invention will result in a significantly increased selectivity for monoalkylation of the aromatic compound to the desired product whether it be a monoalkylated product or a polyalkylated product.

The alkylation process of the invention is typically carried out by passing the reactants through one or more fixed beds of the catalyst of the invention. An excess of the aromatic compound is utilized in order to minimize the formation of polymers of the alkylating agent and undesired polyalkylated products. The alkylating agent is essentially completely consumed in the process and the reactor effluent is fractionated to recover the unreacted aromatic compound for recycle, the desired alkylated product, and any minor proportion of undesired polyalkylated product which may be recycled to the alkylation reactor to suppress any net production of undesired polyalkylated compounds. In some cases it may be desired to use a multistage system of alkylation reactors in lieu of a single reactor.

The alkylation process is normally carried out at a temperature between about 200° F. and about 900° F., preferably between about 300° F. and 600° F. The pressure utilized in the process ranges between about 150 p.s.i.g. and 2000 p.s.i.g., preferably between about 400 p.s.i.g. and 1500 p.s.i.g. The weight hourly space velocity typically ranges between about 2 and 2000, preferably between about 4 and 100. The mole ratio of the alkylating agent to the aromatic compound used typically ranges between about 0.01 and 1.0, preferably between about 0.02 and 0.1.

The nature and objects of the invention are further illustrated b the following example which is provided for illustrative purposes only and not to limit the invention as defined by the claims. The example demonstrates that the selectivity for monoalkylation of an alkylation catalyst can be significantly increased by first depositing carbonaceous material on the catalyst to suppress its alkylation activity and subsequently removing the carbonaceous material from the catalyst by combustion.

EXAMPLE

Fifty grams of a fresh alkylation catalyst are placed in the form of a fixed bed in a pilot plant size reactor vessel. The catalyst is in the shape of 1/16 inch cloverleaf pellets containing 90 weight percent LZY-82 zeolite and 10 weight percent Catapal alumina. Benzene and propylene are passed upwardly through the bed at ambient temperature and at a rate of 51 grams per hour and 6.9 grams per hour, respectively. The temperature in the reactor vessel is raised to 325° F. while the flows of benzene and propylene are continued at constant rates. The pressure in the reactor is maintained at about 500 p.s.i.g. and the weight hourly space velocity is 1.14. The temperature profile of the catalyst bed is monitored on a daily basis. The initial exotherm temperature at the inlet of the bed ranges between 338° F. and 342° F. while the average bed temperature is about 325 ° F. The process conditions for the remainder of the run are set forth below in Table 1.

TABLE 1

| Run Time (hours) | Benzene Flow (grams/hr) | Propylene Flow (grams/hr) | Exotherm Temp. (°F.) |
|---|---|---|---|
| 0–240 | 51–53 | 6.9–10.3 | 340–348 |
| 240–360 | 50–53 | 13.6–13.8 | 351–356 |
| 360–790 | 100–108 | 26.5–33.5 | 345–365 |

The product from the reactor is analyzed at periodic intervals to determine when complete propylene conversion terminates. Movement of the reaction exotherm zone through the bed is used to monitor for deactivation. After about 700 hours the exotherm zone passes through the bed and propylene is present in the product mixture confirming that the catalyst is essentially deactivated.

After the catalyst is deactivated as described above, benzene is purged from the catalyst bed, and the catalyst is removed from the pilot plant reactor and transferred to a pilot plant size fixed bed apparatus. Here the deactivated catalyst is contacted at a temperature of 850° F. with a gas stream prepared by blending air and nitrogen in a ratio such that the resultant gas contains about 0.5 volume percent oxygen. The oxygen concentration of the gas is then increased to 2.0 volume percent and the contacting continued until breakthrough of oxygen is detected. The catalyst bed is gray in color after the above treatment indicating an incomplete removal of carbon. To obtain complete removal of carbon, the temperature in the fixed bed unit is raised to 950° F. and contacting of the catalyst with the gas containing 2.0 volume percent oxygen is continued until the color of the catalyst particles becomes a light tan. The physical properties of the fresh catalyst are compared with those of the catalyst treated in the above-described fashion in Table 2 below.

TABLE 2

| | Fresh Catalyst | Treated Catalyst |
|---|---|---|
| Surface Area ($m^2$/gm) | 691 | 666 |
| % Crystallinity | 54 | 53 |
| Unit Cell Dimension (Angstroms) | 24.499 | 24.464 |
| Crush Strength (lbs) | 11 | 10 |
| Color | white | light tan |

The selectivity of the fresh catalyst as compared to the treated catalyst is determined as described below. Ten grams of the catalyst treated as discussed above are placed in the form of a fixed bed in the pilot plant size reactor vessel utilized to deactivate the fresh catalyst. Propylene and benzene are passed upwardly through the catalyst bed in a molar ratio of 0.033, propylene to benzene, at a temperature of 325° F. and a pressure of 500 p.s.i.g. The weight hourly space velocity is 10. Liquid and vapor samples from the outlet of the reactor are analyzed periodically over the length of the run. The run is terminated after 900 hours as no decline in activity or change in selectivity of the catalyst is noted. The product at the end of the run is analyzed and the cumene selectivity calculated. The resultant data are set forth below in Table 3 and compared with similar data obtained under identical conditions when using the fresh catalyst instead of the treated catalyst.

TABLE 3

COMPARISON OF PRODUCT YIELDS

| Product | Fresh Catalyst (molar %) | Treated Catalyst (molar %) |
|---|---|---|
| Cumene | 94.63 | 97.58 |
| 1,3 Diisopropyl Benzene | 2.69 | 0.984 |
| 1,2 Diisopropyl Benzene | 0.23 | 0.085 |
| 1,4 Diisopropyl Benzene | 2.128 | 0.499 |
| 1,3,5 Triisopropyl Benzene | 0.068 | 0.060 |
| Isopropyl Indane | 0.063 | — |
| 1,2,4 Triisopropyl Benzene | 0.052 | — |
| Diphenyl-Propane | 0.139 | 0.065 |
| Methyl-Isopropyl Indane | — | 0.123 |
| Cumene Dimer | — | 0.604 |
| Cumene Selectivity* | 94.6% | 97.6% |

*Cumene selectivity = 100 × [(molar amount of cumene)/(molar amount of cumene + the molar amount of all other propylene derived products)].

As can be seen from Table 3, the yield of cumene is significantly higher using the treated catalyst as opposed to the fresh catalyst. The cumene selectivity if 97.6% for the treated catalyst as compared to 94.6% for the fresh catalyst, an increase of 3 percentage points. Such an increase in selectivity is quite significant when commercial operations for the production of cumene by the alkylation of benzene with propylene are considered. The higher selectivity for cumene is due to a marked reduction in the formation of 1,3 and 1,4 diisopropyl benzene. It is theorized that the decrease in the production of the dialkylated product may be caused by passivation of active acid sites, the generation of new sites with a net lower acidity or a reduction in the ability of the catalyst to adsorb cumene.

Although this invention has been primarily described in conjunction with an example and by reference to embodiments thereof, it is evident that many alternatives, modifications and variations will be apparent to those skilled in the art in light of the foregoing description. Accordingly, it is intended to embrace within the invention all such alternatives, modifications and variations that fall within the spirit and scope of the appended claims.

We claim:

1. A process for treating an alkylation catalyst comprising a molecular sieve having catalytic activity for alkylation and a porous, inorganic refractory oxide, said alkylation catalyst being substantially devoid of hydrogenation metal components, to increase the selectivity of said alkylation catalyst for monoalkylation which comprises:

(a) depositing carbonaceous material on said catalyst in such a manner as to suppress the alkylation activity of said catalyst; and (b) contacting the carbon-containing catalyst particles formed in step (a) with a gaseous oxidizing agent at an elevated temperature to remove at least a portion of said carbonaceous material so as to increase the selectivity of said alkylation catalyst for monoalkylation by at least about 1.0 percentage point.

2. A process as defined by claim 1 wherein said carbonaceous material is deposited on said catalyst by contacting said alkylation catalyst in a contacting zone with a feedstock comprising at least one organic compound.

3. A process as defined by claim 2 wherein said molecular sieve having catalytic activity for alkylation is a nonzeolitic molecular sieve.

4. A process as defined by claim 2 wherein said molecular sieve having catalytic activity for alkylation is a zeolitic molecular sieve.

5. A process as defined by claim 4 wherein said zeolitic molecular sieve comprises a Y zeolite.

6. A process as defined by claim 5 wherein said Y zeolite comprises LZY-82 zeolite.

7. A process as defined by claim 4 wherein said zeolite molecular sieve is selected from the group consisting of fluorided Y zeolites, X zeolites, zeolite beta, zeolite L and zeolite omega.

8. A process as defined by claim 6 wherein said porous, inorganic refractory oxide comprises alumina.

9. A process as defined by claim 2 wherein said feedstock comprises a hydrocarbon feedstock.

10. A process as defined by claim 9 wherein said hydrocarbon feedstock comprises a $C_2$–$C_{15}$ alkene or alkyne.

11. A process as defined by claim 9 wherein said hydrocarbon feedstock comprises a mixture of an aromatic compound and an olefin and said alkylation catalyst is contacted with said feedstock under conditions such that said aromatic compound reacts with said olefin.

12. A process as defined by claim 9 wherein said gaseous oxidizing agent consists essentially of air and nitrogen or air and carbon dioxide.

13. A process as defined by claim 9 wherein said gaseous oxidizing agent comprises oxygen.

14. A process as defined by claim 13 wherein said gaseous oxidizing agent comprises between about 0.05 volume percent and about 5.0 volume percent oxygen.

15. A process as defined by claim 9 wherein the carbon-containing catalyst particles formed in step (a) are contacted with a gaseous oxidizing agent comprising between about 0.05 and about 5.0 volume percent oxygen at a temperature between about 750° F. and about 1100° F. to remove a portion of said carbonaceous material and produce catalyst particles of reduced carbon content, the oxygen content of said gaseous oxidizing agent is increased at least about 0.01 percentage point, and the catalyst particles of reduced carbon content are contacted with said gaseous oxidizing agent of increased oxygen content at a temperature between about 850° F. and about 1200° F. until substantially all of said carbonaceous material is removed.

16. A process as defined by claim 9 wherein greater than about 95 weight percent of said carbonaceous material is removed in step (b).

17. A process as defined by claim 9 wherein said alkylation catalyst is a fresh catalyst and is treated in accordance with steps (a) and (b) prior to being used to produce alkylated aromatics.

18. A process as defined by claim 9 wherein said alkylation catalyst forms a fixed bed in said contacting zone and is contacted with said feedstock until the reaction exotherm zone has passed through said fixed bed of catalyst.

19. A process for treating an alkylation catalyst comprising a molecular sieve having catalytic activity for alkylation and a porous, inorganic refractory oxide, said alkylation catalyst being substantially devoid of hydrogenation metal components, to increase the selectivity of said alkylation catalyst for monoalkylation, the alkylation activity of said catalyst having been suppressed by the deposition of carbonaceous material thereon to form carbon-containing catalyst particles, which process comprises contacting said carbon-containg catalyst particles with a gaseous oxidizing agent at an elevated temperature to remove at least a portion of said carbonaceous material so as to increase the selectivity of said alkylation catalyst for monalkylation by at least about 1.0 percentage point.

20. A process as defined by claim 19 where in said molecular sieve having catalytic activity for alkylation comprises a Y zeolite prepared by the process comprising:

(a) ammonium exchanging a Y zeolite to a sodium content between about 0.6 and 5.0 weight percent, calculated as $Na_2O$;

(b) calcining the ammonium-exchanged zeolite at a temperature between about 600° F. and 1650° F. in the presence of steam at a water vapor partial pressure greater than about 2.0 p.s.i.a. to reduce the unit cell size of the ammonimm-exchanged zeolite to a value in the range between about 24.40 and 24.64 Angstroms; and (c) ammonium exchanging the steam calcined zeolite to replace at least 25 percent of the residual sodium ions and obtain a zeolite product of less than about 0.6 weight percent sodium, calculated as $Na_2O$.

21. A process as defined by claim 19 wherein said molecular sieve having catalytic activity for alkylation comprises LZY-82 zeolite.

22. An alkylation catalyst having an increased selectivity for monoalkylation made by treating an alkylation catalyst substantially devoid of hydrogenation metal components in accordance with the process of claim 19, wherein said alkylation catalyst substantially devoid of hydrogenation metal components comprises a molecular sieve having catalytic activity for alkylation and a porous, inorganic refractory oxide.

23. An alkylation catalyst as defined by claim 22 wherein the particles of said alkylation catalyst have a shape such that the surface-to-volume ratio of said particles is greater than that of a cylinder.

24. A process as defined by claim 1 wherein there is substantially no decrease in the crystallinity of said molecular sieve while said carbon-containing catalyst particles are contacted with said gaseous oxidizing agent.

25. A process for treating an alkylation catalyst consisting essentially of a molecular sieve having catalytic activity for alkylation and at least one porous, inorganic refractory oxide to increase the selectivity of said alkylation catalyst for monoalkylation by at least about 1.0 percentage point which comprises:

(a) depositing carbonaceous material on said catalyst in such a manner as to suppress the alkylation activity of said catalyst;

(b) contacting the carbon-containing catalyst particles formed in step (a) with a gaseous oxidizing agent comprising between about 0.05 and about 5.0 volume percent oxygen at a temperature between about 750° F. and about 1100° F. to remove a portion of said carbonaceous material and produce a first set of catalyst particles having a reduced carbon content;

(c) increasing the oxygen content of said gaseous oxidizing agent by at least about 0.05 percentage point;

(d) contacting said first set of catalyst particles having a reduced carbon content with said gaseous oxidizing agent of increased oxygen content at about the temperature utilized in step (b) to remove a further portion of said carbonaceous material and produce a second set of catalyst particles having a reduced carbon content as compared with said first set of catalyst particles; and (e) contacting said second set of catalyst particles with said gaseous oxidizing agent at a temperature between about 850° F. and about 1200° F. that is higher than the temperature used in step (b) while maintaining the oxygen concentration in said gaseous oxidizing agent as about the value used in step (d) until substantially all of said carbonaceous material is removed from said catalyst particles.

26. A process as defined by claim 25 wherein said molecular sieve having catalytic activity for alkylation comprises LZY-82 zeolite.

27. A process for treating an alkylation catalyst consisting essentially of a molecular sieve having catalytic activity for alkylation and at least one porous, inorganic refractory oxide to increase the selectivity of said alkylation catalyst for monoalkylation which comprises:

(a) depositing carbonaceous material on said catalyst in such a manner as to suppress the alkylation activity of said catalyst; and (b) contacting the carbon-containing catalyst particles formed in step (a) with a gaseous oxidizing agent at an elevated temperature to remove at least a portion of said carbonaceous material so as to increase the selectivity of said alkylation catalyst for monoalkylation by at least about 1.0 percentage point.

28. A process as defined by claim 11 wherein said aromatic compound comprises benzene and said olefin comprises propylene.

29. An alkylation catalyst having an increased selectivity for monoalkylation made by treating an alkylation catalyst substantially devoid of hydrogenation metal components in accordance with the process of claim 28, wherein said alkylation catalyst substantially devoid of hydrogenation metal components comprises a molecular sieve having catalytic activity for alkylation and a porous, inorganic refractory oxide.

30. A process as defined by claim 19 wherein said carbonaceous material is deposited on said alkylation catalyst by contacting said catalyst in a contacting zone with a feedstock comprising a mixture of an aromatic compound and an olefin under conditions such that said aromatic compound reacts with said olefin.

31. A process as defined by claim 30 wherein said aromatic compound comprises benzene and said olefin comprises propylene.

32. A process as defined by claim 26 wherein said carbonaceous material is deposited on said alkylation catalyst by contacting said catalyst in a contacting zone with a feedstock comprising a mixture of an aromatic compound and an olefin under conditions such that said aromatic compound reacts with said olefin.

33. A process as defined by claim 32 wherein said aromatic compound comprises benzene and said olefin comprises propylene.

34. A process for treating an alkylation catalyst comprising a molecular sieve having catalytic acitivity for alkylation and a porous, inorganic refractory oxide, said alkylation catalyst being substantially devoid of hydrogenation metal components, to increase the selectivity of said alkylation catalyst for monoalkylation by at least about 1.0 percentage point, the alkylation activity of said catalyst having been suppressed by the deposition of carbonaceous material thereon to form carbon-containing catalyst particles, which process comprises:

(a) contacting said carbon-containing catalyst particles with a gaseous oxidizing agent comprising between about 0.05 and about 5.0 volume percent oxygen at a temperature between about 750° F. and about 1100° F. to remove a portion of said carbonaceous material and produce a first set of catalyst particles having a reduced carbon content;

(b) increasing the oxygen content of said gaseous oxidizing agent by at least about 0.05 percentage point;

(c) contacting said first set of catalyst particles having a reduced carbon content with said gaseous oxidizing agent of increased oxygen content at about the temperature utilized in step (a) to remove a further portion of said carbonaceous material and produce a second set of catalyst particles having a reduced carbon content as compared with said first set of catalyst particles; and (d) contacting said second set of catalyst particles with said gaseous oxidizing agent at a temperature between about 850° F. and about 1200° F. that is higher than the temperature used in step (a) while maintaining the oxygen concentration in said gaseous oxidizing agent at about the value used in step (c) until substantially all of said carbonaceous material is removed from said catalyst particles.

35. A process as defined by claim 34 wherein said molecular sieve having catalytic activity for alkylation comprises a Y zeolite.

36. A process as defined by claim 35 wherein said Y zeolite comprises LZY-82 zeolite.

37. An alkylation catalyst having an increased selectivity for monoalkylation made by treating an alkylation catalyst substantially devoid of hydrogenation metal components in accordance with the process of claim 35 wherein said alkylation catalyst substantially devoid of hydrogenation metal components comprises a Y zeolite having catalytic activity for alkylation and a porous, inorganic refractory oxide.

38. A process as defined by claim 36 wherein the gaseous oxidizing agent used in step (a) comprises about 0.5 volume percent oxygen and the gaseous oxidizing agent of increased oxygen content used in step (c) comprises about 2.0 volume percent oxygen.

* * * * *